United States Patent [19]

Bokros et al.

[11] 4,015,601
[45] Apr. 5, 1977

[54] BLOOD ACCESS DEVICE

[75] Inventors: Jack C. Bokros; Victor Slivenko, both of San Diego, Calif.

[73] Assignee: General Atomic Company, San Diego, Calif.

[22] Filed: Oct. 14, 1975

[21] Appl. No.: 622,090

[52] U.S. Cl. .............................. 128/214 R; 128/348
[51] Int. Cl.$^2$ .......................................... A61M 5/00
[58] Field of Search ........... 128/1 R, 214 R, 334 R, 128/348, 350 R

[56] References Cited
UNITED STATES PATENTS

| | | | |
|---|---|---|---|
| 2,935,068 | 5/1960 | Donaldson | 128/348 |
| 3,505,991 | 4/1970 | Hellerstein et al. | 128/1.1 |
| 3,663,965 | 5/1972 | Lee et al. | 128/348 X |
| 3,765,032 | 10/1973 | Palma | 128/348 X |
| 3,783,868 | 1/1974 | Bokros | 128/348 X |
| 3,815,577 | 6/1974 | Bucalo | 128/1 R |

Primary Examiner—Dalton L. Truluck
Attorney, Agent, or Firm—Fitch, Even, Tabin & Luedeka

[57] ABSTRACT

A device to provide access to the circulatory system of a living body includes a conduit and a housing integrally associated with the conduit and having fluid communication therewith through an aperture in a wall common to both. The housing extends the fluid communication to a point outside the living body. Inside the housing is a movable valve body which has a port alignable with the aperture. The valve body is movable in the housing between positions of alignment and non-alignment of the aperture and the port to selectively establish fluid communication between the circulatory system and the outside of the living body. At least the surfaces of all parts of the device that contact blood and tissue are made of biologically compatible material.

12 Claims, 5 Drawing Figures

U.S. Patent  April 5, 1977  4,015,601
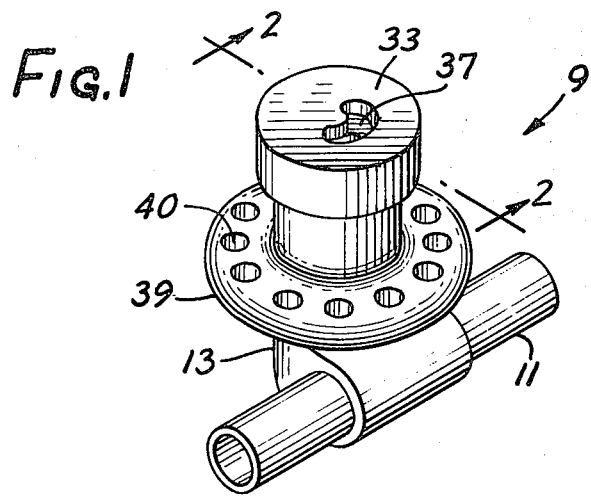
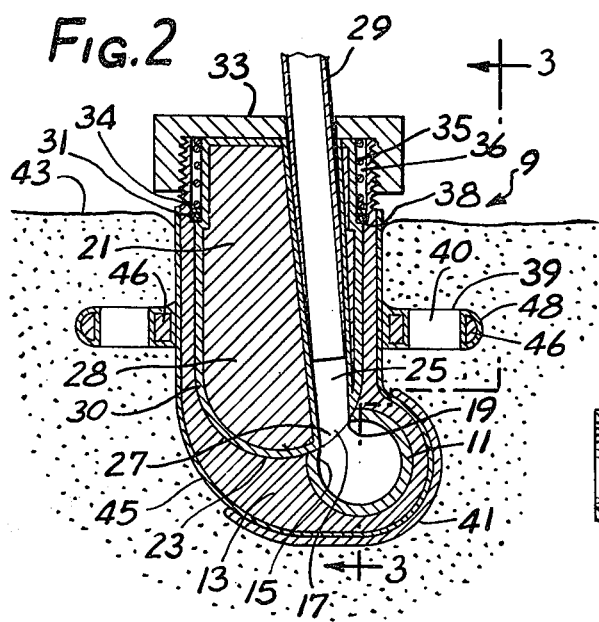
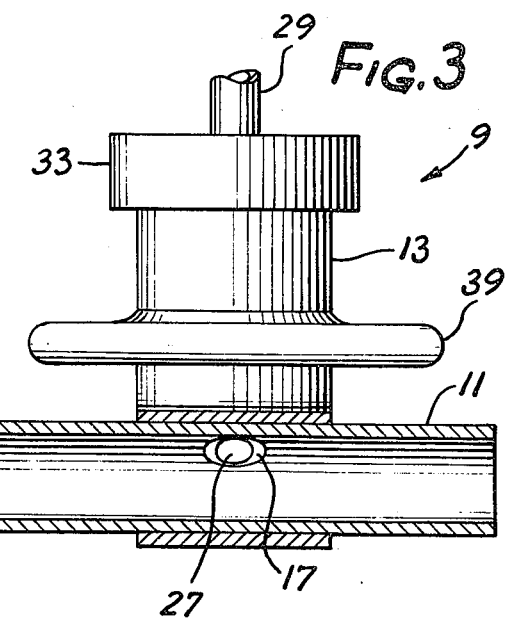
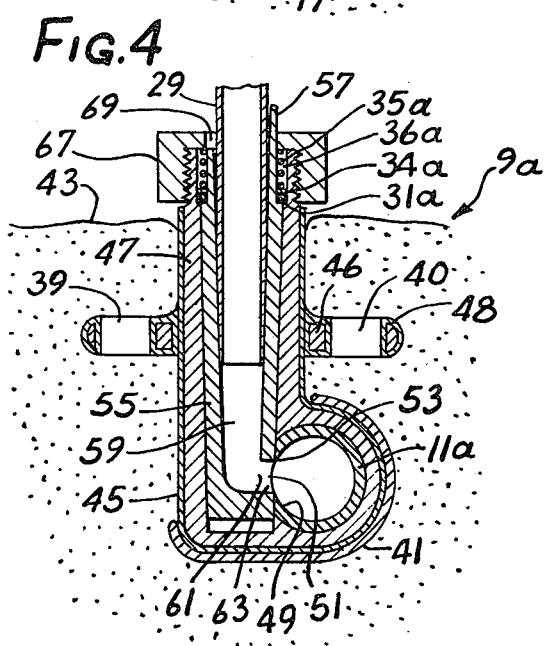
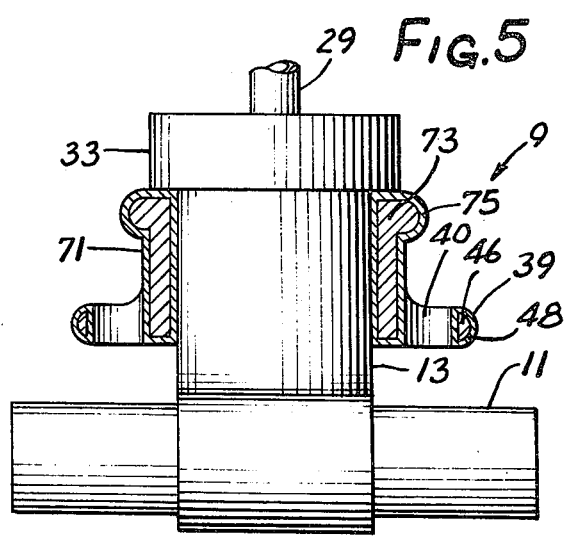

BLOOD ACCESS DEVICE

This invention relates to medical devices and, more particularly, to a device to provide access to the circulatory system of a living body.

There is a need for a device to provide access to the circulatory system of a living body in circumstances requiring, for example, repeated withdrawing or injection of blood over a prolonged period of time. Such device, however, should be biologically compatible with the living tissues surrounding it. In this connection, the device should not prevent healing, irritate tissues, or stimulate a prolonged rejection response by the living body. Further, the device should be physiologically inert over prolonged periods of time and should be mechanically strong and reliable.

Accordingly, it is a primary object of this invention to provide a device for insertion into a blood vessel of the circulatory system that will afford access to the blood at any desired time and that is biologically compatible with the living tissues surrounding the device without irritating the tissues.

It is a further object of the invention to provide a device of the aforementioned type that is physiologically inert over prolonged periods of time and is mechanically strong and reliable.

The accomplishment of these and other objects of the invention will become apparent from the following description and its accompanying drawings of which:

FIG. 1 is a perspective view of a blood access device embodying various features of the invention and adapted for insertion in a blood vessel;

FIG. 2 is a cross-sectional view of the device of FIG. 1 taken along the line 2—2 and showing the device in the environment of a living body and illustrating parts aligned for fluid communication;

FIG. 3 is a side view taken along the line 3—3 of FIG. 2;

FIG. 4 is a view similar to FIG. 2 and showing an alternative form of the device of FIG. 1 in the environment of a living body; and FIG. 5 is a side view of the device of FIG. 1 showing a modification on the exterior thereof.

The device of the invention includes two principal outer portions generally at right angles to one another. One portion is tubular with open ends and is intended for insertion longitudinally in a blood vessel, and the other portion is a housing with one open end and containing a valve for establishing fluid communication with the blood in the blood vessel. The valve is adapted to receive a catheter which is used to establish a blood flow line, and the blood may flow either into the blood vessel or out of the blood vessel. The device is structured of materials that are biologically compatible with the blood and tissues of a living body in which it is inserted. All blood contacting surfaces are carbon. Further, the material is physiologically inert over prolonged periods of time and is mechanically strong and reliable, all of which are described in detail hereinafter.

Referring now to FIG. 1, there is shown a blood access device 9 having a conduit 11 and a housing 13 adjoining the conduit 11. In this illustrated embodiment both the conduit 11 and the housing 13 are round tubular structures, the conduit 11 being open-ended and the housing 13 being closed at one end and open at the other. The conduit 11 and the housing 13 adjoin one another in a transverse relation.

In FIG. 2 it will be seen that a common wall 15 is intermediate the interiors of the conduit 11 and the housing 13. Through the common wall 15 is an aperture 17 which provides fluid communication between the two interiors. The aperture 17 is defined by a perimeter formed of a sharp edge 19 of the common wall 15.

A valve body 21 is in the housing 13 and is generally in the form of a cylinder having a hemispherical end 23. The valve body and hemispherical end are in a snug or close-fitting relation with the internal portion of the housing 13. Nonetheless, the valve body is coaxially rotatable within the housing. The valve body is solid except for a longitudinal passage 25 at an angle to the axis of the valve body and terminates in a port 27. In the illustrated embodiment, the longitudinal passage 25 is located in the housing 13 so as to align the port 27 with the aperture 17 when the valve body is in a given axially rotative position to establish fluid communication between the conduit 11 and the housing 13. The inner surface of this longitudinal passage is tapered to a smaller inner diameter at the port end. Preferably, the valve body 21 comprises a solid graphite core 28 and a pyrolytic carbon coating 30, as fully described hereinafter.

The longitudinal passage 25 receives a catheter 29 to complete a flow path for the blood when a blood passage is established by alignment of the port 27 and the aperture 17 in accordance with the invention. The catheter 29 is tapered on its end outer surface to complement the interior of the longitudinal passage.

A cap 33 is applied over the open end of the housing 13 and a compression means 35, such as a spring or packing is provided under the cap, all to retain the valve body 21 in a seated position in the housing. As best seen in FIG. 1, the cap 33 is provided with an orifice 37 in the form of a curvilinear slot having a length less than a full circle. Preferably, the length of the slot is equivalent to one-quarter of a circle to permit a one-quarter turn of the valve body 21, and the cap 33 is of a screw type constructed of a material such as stainless steel. The compression means 35 may be a coil type compression spring or packing that fits in a recess 36 between the underside of the cap 33 and a shoulder 38 near the top of the valve body 21. The compression means applies a steady pressure against the valve body 21.

In the bottom of the recess 36 over the upper edge of the interface between the valve body 21 and the housing 13 is a bacterial seal in the form of an "O" ring 31, made of an elastomeric material. This provides a barrier against an invasion of bacteria from the recess 36 down the device between the valve and the housing. Over the "O" ring 31 is a flat metallic ring 34 which serves as a base for the compression means 35. The "O" ring 31 adds to the compressive force applied to the shoulder 38 of the valve body 21. Alternatively, the compression means 35 and bacterial seal combination could be in the form of two "O" rings separated by a teflon ring. The teflon ring should be long enough for the combination to completely fill the recess 36 and provide compression under the cap 33. In such instance, the spring or packing could be omitted.

The catheter 29 is inserted through the orifice 37 and into the longitudinal passage when the valve is closed, i.e., the port 27 is in a non-aligned relation with the aperture 17. To establish a passage for blood in accordance with the invention, the catheter 29 is used as a handle to rotate the valve body 21 within the limits of the orifice 37 to align the port 27 with the aperture 17. After such rotation, the valve is open and a passage for blood is established. The blood may flow in either direction in this passage as circumstances direct.

To interrupt the blood passage, the valve body 21 is rotated at least one-quarter of a turn so that the port 27 is nonaligned with the aperture 17. In this condition, a rounded portion of the hemispherical end 23 of the valve body 21 completely covers the aperture 17, and because of the close-fitting, seated relation of the valve body with the wall of the conduit 11, there is a liquid and bacterial seal established around the sharp edge 19, as described hereinafter. The bacterial seal is a further barrier to the invasion of bacteria in the blood stream.

Around the perimeter of the housing 13 is a stabilizing flange 39 which forms a collar that projects outwardly from the housing and carries a plurality of holes 40. This flange 39 may be made of rough carbon or other compatible material, also as described hereinafter. Body tissue will grow in and around the holes 40 and stabilize the position of the blood access device 9. The position of the flange 39 may be movable on the housing to control the extent the housing extends beyond the surface of the skin, or the position of the flange may be fixed if uniformity of housing height above the flange is found to be desirable. Further, it may be desirable to also include an epithelium stopping means in the form of another collar (not shown) above the flange, as described in U.S. Pat. No. 3,783,868, issued Jan. 8, 1974, to inhibit the progressive growth of epithelium tissue down and around the housing 13.

In FIG. 2, the device 9 is illustrated as being implanted in a living body, and the conduit 11 is shown in an inserted relation with a blood vessel, such as an artery 41. It should be recognized that although the blood access device 9 is useful in a living human body, it may also have veterinary or scientific applications in other living animals, domestic or wild. Further, although its use is shown in an artery, it should be understood that this is for illustration only and that the device of the invention may be inserted in any part of a circulatory system as needed, and there is no intention of limiting its use to an artery.

The device 9 is inserted in the living body by any suitable surgical procedure. Generally, a longitudinal incision is made through the skin at the desired location for insertion in the blood vessel, and an incision is made in the blood vessel after momentarily stopping the flow of blood therethrough. Sutures are then used to sew up the blood vessel after the ends of the conduit 11 have been inserted therein, and other sutures are used to sew up the skin around the housing 13. In this connection, it is noted that the length of the housing 13 above the point of association with the conduit 11 is sufficient to extend from the blood vessel in which the conduit 11 is inserted to a point outside the living body, i.e., outside the skin layer 43. This may be approximately 1 cm.

As mentioned previously, because the blood access device 9 is inserted within a living body, it is important that the material of the device be biocompatible (biologically compatible) with the blood and living tissues which surround it. Furthermore, the device, once inserted, should not prevent healing, irritate tissues, or stimulate a strong or prolonged rejection response by the living body, and the material of the device should be physiologoically inert over long periods of time in addition to being mechanically strong and reliable.

In accordance with the invention, a coating of carbon is utilized on all blood contacting surfaces and on the housing/skin interface. This carbon coating may be pyrolytic carbon, vapor-deposited carbon or vitreous carbon, or these kinds of coating may be utilized on different parts of the blood access device 9. Pyrolytic carbon, vitreous (glassy) carbon, and vapor-deposited carbon are compatible with the surrounding tissues over prolonged time periods when inserted through the skin of a living body. Preferably, pyrolytic carbon and/or vapor-deposited carbon are used. These coatings do not tend to irritate the surrounding tissues and they promote the establishment of a barrier to external pathogens.

In general, the preferred construction of the device 9 includes a metallic housing, such as titanium, stainless steel or a chromium-cobalt alloy such as VITALLIUM, and a vapor-deposited carbon coating 45 on the housing. The method of depositing this coating is described hereinafter. The conduit 11 is constructed of pyrolytic carbon and may be formed in any suitable manner, such as deposition of a built-up coating on a mandrel, after which the mandrel is removed, leaving the tube-like structure. The valve body 21 is constructed by preshaping a suitable substrate or core 28 to the form desired for the part, making the passageway 25 through the core material of the valve body, such as by drilling, and applying the pyrolytic carbon coating 30 on the core, including the inner surfaces of the passageway 25. The flange 39 also is constructed on a suitable substrate or core 46 which is preshaped to the desired form, the holes 40 are made therein, such as by drilling, and a pyrolytic carbon coating 48 is applied to the core, including the inner surfaces of the holes 40. Preferably, this carbon coating 48 has a rough finish. The core materials and the process of applying the pyrolytic carbon coatings are described hereinafter.

In joining the conduit 11 and the housing 13, the sidewall of the conduit is opened, as by grinding, so as to provide for a partial intersection thereof by the hemispherical end 23 of the valve body 21. The metallic housing 13 is so closely associated in fit with the conduit 11 as to effectively support the joining of these parts in the illustrated arrangement.

This arrangement allows the forming of a seat in the portion of the conduit wall that receives the hemispherical end of the valve body while at the same time forming the sharp edge 19 around the aperture 17. The seat conforms to a portion of the hemispherical end 23 of the valve body to establish the liquid and bacterial seal around the aperture. The port 27 and longitudinal passage 25 are located so as to align with the aperture 17 when the valve body is appropriately positioned.

As seen in FIG. 3, this arrangement will cause the aperture to have an oval shape. The minor diameter of the aperture is approximately 1 to 3 mm. The inner diameter of the conduit 11 and the housing 13 is from about 4 to about 6 mm. The length of the conduit and housing is from about 1 to about 3 cm.

As mentioned previously, the valve body should have a close-fitting relation with the interior of the housing 13, and the diameter of the valve body should be determined with this in mind so that after the outer surface of the pyrolytic carbon is lapped and polished, the snug or close-fitting relation exists. In this connection, a very important step in making the blood access device 9 is the lapping of the portion of the external surface of the conduit 11 that receives the housing 13 to conform this portion to the hemispherical end of the valve body 21 so as to produce the sharp edge 19 and a seat for the valve. Such a sharp edge does not permit the accumulation and coagulation of blood around the aperture. Thus, after having once established fluid communication between the artery 41 and the catheter 29 and then closing the valve body by rotation thereof, the blood flow will be cleanly interrupted with no places for accumulation or coagulation of the blood in the conduit 11. After the valve is closed, any residual blood in the valve body 21 may be flushed out by using a suitable cleansing solution. Thereafter, a suitable plug (not shown) may be inserted in the open, upper end of the longitudinal passage to keep the interior clean until next use.

The pyrolytic carbon may be deposited upon the mandrel in the instance of the conduit 11 and upon the formed substrate in the instance of the valve body 21 in the manner described in U.S. Pat. No. 3,783,868 and U.S. Pat. No. 3,298,921. Preferably, the pyrolytic carbon is deposited on the substrates so as to build up a wall thickness of approximately 500 microns. An example of a coating method that may be employed to obtain such thickness is that of supporting the formed substrate on a rotating or stationary mandrel within a large fluidized bed, as discussed in the aforementioned patents, or coating on freely moving rods in a fluid bed.

Pyrolytic carbon is, by definition, deposited by the pyrolysis of a carbon-containing substance. Accordingly, the core material on which the pyrolytic carbon is deposited will be subject to the fairly high temperatures necessary for pyrolysis. Generally, hydrocarbons are employed as the carbon-containing substance to be pyrolyzed, and temperatures of at least about 1000° C are used. Some examples of deposition of pyrolytic carbon are set forth in the aforementioned U.S. Pat. No. 3,298,921. Processes illustrated and described in this patent employ methane as the source of carbon and utilize temperatures generally in the range of about 1200° C to 2300° C. Although it is possible to deposit pyrolytic carbon having the desired properties with regard to this invention at somewhat lower temperatures by using other hydrocarbons, for example, propane or butane, it is generally considered that the core materials should remain substantially stable at temperatures of at least about 1000° C and preferably at even higher temperatures. Pyrolytic carbons deposited at temperatures below about 1500° C are particularly suited for use in the blood access device 9, because such pyrolytic carbons have exceptional tissue compatibility and mechanical reliability.

Examples of core materials which have the aforementioned stability at high temperatures include artificial graphite, boron carbide, silicon carbide, refractory metals (and alloys), such as tantalum, titanium, molybdenum, tungsten, and various ceramics, such as mullite. A preferred substrate material is polycrystalline graphite. An example of such a graphite is the polycrystalline graphite sold under the trademark POCO.

The metallic housing may be formed by a known machining process, and the vapor-deposited carbon coating 45 may be applied by the process described in United States patent application "Biocompatible Carbon Prosthetic Devices", Ser. No. 527,971, filed Nov. 29, 1974 and assigned to the same assignee as the instant application. As generally described therein a substrate is placed in an evaporative coater and a vacuum is established. A crucible within the coater, filled with a commercial grade of artificial graphite, is heated by electron beam bombardment. Coating is carried out until the desired thickness of carbon is deposited and the substrate is then removed. In the illustrated embodiment, this thickness is about 0.5 micron. This process results in an exterior carbon layer that is smooth and uniform.

Referring now to FIG. 4, there is shown an alternative embodiment 9a of the blood access device 9. A conduit 11a is a round tubular structure, open-ended, and intended for insertion in a blood vessel in the same manner as the conduit 11 of the device 9. This conduit 11a adjoins a housing 47 along the sidewall of the housing. The interiors of the two are separated by a wall 49 common to both. In the common wall is an aperture 51 that provides fluid communication between the two interiors and is defined by a perimeter formed by a sharp edge 53 of the common wall.

In the housing 47 is a valve body 55. At least the interior surface of the housing 47 is tapered as indicated, and at least the outer surface of the valve body 55 is tapered in a complementary manner to the housing interior. These complementary tapered surfaces afford a very close-interfitting relationship. Nonetheless, the valve body 55 is movable within the housing. Specifically, in this illustrated alternative form 9a, the valve body and the housing are coaxially related, and the valve body is rotatable about the axis in the housing.

Facilitating this rotation is means such as a boss 57 provided in an eccentric location on the outer end of the valve body 55. This boss 57 provides a gripping means for manually rotating the valve body.

The valve body 55 is generally in the form of a pyrolytic carbon cylinder having a lower closed end and a longitudinal passage 59 parallel to the common axis and a transverse passage 61 at an angle thereto terminating in a port 63. Specifically in the device 9a, the longitudinal passage 59 is located coaxially of the housing 47 and its inner surface is tapered to a smaller inner diameter at the transverse passage end. The transverse passage 61 is located so as to align the port 63 with the aperture 51 in a given axially rotative position of the valve body 55 to establish fluid communication between the conduit 11a and the valve 55 in the housing 47. The longitudinal passage 59 receives the catheter 29 in completing a flow path for the blood. Preferably, the catheter is tapered on its end outer surface to complement the interior of the longitudinal passage. Blood flow is established by aligning the port and the aperture in accordance with the invention.

The catheter is inserted in the longitudinal passage when the valve is closed, i.e., the port 63 is in a non-aligned relation with the aperture 51. To establish a passage for blood in accordance with this alternative form of the invention, the device 9a is inserted in a living body with the conduit 11a being inserted in a blood vessel, such as the artery 41 in the same manner as described previously in connection with the device 9. The catheter 29 is inserted in the longitudinal passage 59, and the valve body 55 is rotated manually by using the boss 57 to align the port and the aperture. This boss 57 is located directly over the port 63 so that the rotative position of the port can always be determined by observation even though the port itself is not visible. Because of the relatively small size of the blood access device 9a, an instrument, such as tweezers, may be advantageously used to grip the boss 57 for rotation. Blood may flow in either direction in the established passage as circumstances direct. To interrupt the blood flow, the valve body 55 is rotated at least one-quarter of a turn so that the port 63 is non-aligned with the aperture 51. In this condition, a portion of the outer surface of the tapered sidewall of the valve body 55 completely covers the aperture 51 and establishes a liquid and bacterial seal therearound. To facilitate this seal, the valve body extends below the aperture to provide additional surface in close-fitting relation with the interior of the housing 47. The narrow end of the valve body does not bottom on the inside of the housing. There is clearance to assure adequate seating of the valve body within the housing along the tapered interface in forming the liquid and bacterial seal. Some slight differences in diameters of the respective parts can be tolerated with this tapered structure.

For hygienic purposes, the interior of the valve should be flushed out with a cleansing solution regularly.

A cap 67 is applied over the open end of the housing 47 to retain the valve body 55 in position in the housing. The cap is provided with an orifice 69 in the form of a circle having a diameter sufficiently large to accommodate the catheter 29 and the eccentrically located boss 57 when the cap is on the housing 47 as illustrated in FIG. 4. Preferably, this cap 67 is a screw-on type made of a suitable material, such as stainless steel.

Compression means 35a in a recess 36a over a flat ring 34a and an "O" ring 31a (bacterial seal) are provided in a manner similar to that described in connection with corresponding portions of the blood access device 9. Also, the alternative form of two "O" rings separated by a teflon ring as previously described could be utilized here. A stabilizing flange 39 having holes 40 is provided around the perimeter of the housing also in a manner similar to that described in connection with the device 9. The body tissue grows in and around the holes 40 to stabilize the position of the device 9a. The flange may be movable or fixed as described previously.

In general, the device 9a is constructed in a manner similar to that described in connection with the device 9, i.e., the housing machined from one of several possible metals, preferably titanium, the pyrolytic carbon conduit prepared on a mandrel and the valve body prepared of a graphite core and a pyrolytic carbon coating thereon. In this valve body, however, the graphite is removed, as by drilling, leaving a pyrolytic carbon shell. The interfacial surfaces of the tapered portions are lapped and polished to enhance the close-fit relation.

An important step in constructing this alternative form 9a of the blood access device is the lapping of the outer surface of a portion of the conduit wall 11a adjacent the lower end of the valve body 55 in the housing 47 to provide the sharp edge 53 that defines the aperture 51. As described previously in connection with the device 9, such a sharp edge does not allow the accumulation and coagulation of blood around the aperture. Thus, after having once established fluid communication between the artery 41 and the catheter 29 and then closing the valve by rotating the valve body 55, the blood flow will be cleanly interrupted with no places for accumulation or coagulation of the blood in the conduit 11a. When the valve is closed and the catheter removed, any residual blood in the longitudinal passage 59 and the transverse passage 61 is flushed out by using a suitable cleansing solution. Thereafter, a suitable plug (not shown) may be inserted in the upper end of the longitudinal passage to keep the interior clean until next use.

In FIG. 5 a blood access device 9 is shown having a modification on the exterior of the housing 13. As previously mentioned, it is important that the material of the device 9 be biologically compatible with the living tissues which surround it. The vapor-deposited carbon coating 45 (FIG. 2) is provided on the metallic housing 13 for this purpose, especially at the housing/skin interface. Such a coating is about 0.5 micron thick, and the strength of this coating can be enhanced at the skin interface by applying a pyrolytic carbon sleeve 71 (FIG. 5) on the outer surface of the housing 13. This sleeve of pyrolytic carbon may be formed on a mandrel in the same manner as the conduit 11 described previously, or a formed substrate 73 of graphite with a pyrolytic carbon coating 75 thereon as described previously, and a suitable cement, such as a medical grade silicone rubber, can be used to secure its position on the housing. The stabilizing flange 39 would encircle the sleeve 71 when the sleeve is so utilized. Alternatively, the flange may be cemented to the sleeve and the sleeve left uncemented on the body so as to be movable longitudinally for small adjustments in position of the housing with respect to the skin surface 43.

Summarizing, there has been described a device for providing access to the circulatory system, which device is biologically compatible with the living tissues which will surround it. The device does not prevent healing, irritate tissues, or stimulate a strong or prolonged rejection response by the living body. Further, the device is physiologically inert over long periods of time and is mechanically strong and reliable.

While the invention has been described in connection with a preferred embodiment and an alternative form, other alternatives, modifications, and variations may be apparent to those skilled in the art in view of the foregoing description. Accordingly, it is intended to embrace all such alternatives, modifications, and variations as fall within the spirit and scope of the appended claims.

What is claimed is:

1. A device to provide access to the circulatory system of a living body comprising a tubular conduit of generally circular cross section insertable in a living blood vessel; a generally cylindrical housing having one end closed and extending transversely of and adjoining said conduit, the point of adjoining being spaced from the housing axis, said housing having fluid communication with said conduit through an aperture in a wall common to both, the perimeter defining said aperture being formed of a sharp edge of the wall, said housing having a length sufficient to extend from the blood vessel to a point outside the living body; a valve body in said housing, said valve body having therein a port alignable with said aperture, said valve body being adapted to receive a catheter in fluid communication with said port, and said valve body being coaxially rotatable in said housing between positions of alignment and non-alignment of said aperture and said port to selectively establish fluid communication between the circulatory system and a catheter inserted in said valve body; and at least all blood and tissue contacting surfaces of said device being made of a biologically compatible material.

2. A device in accordance with claim 1 wherein at least the inner surface of the closed end of said housing has a hemispherical form; wherein said housing adjoins said conduit at the hemispherical end of said housing; wherein said valve body is generally cylindrical and has a hemispherical end surface complementary to the inner hemispherical end surface of said housing; and wherein the fluid communication between the port and a catheter inserted in said valve body occurs through a longitudinal passageway therebetween passing through said valve body at an angle to the axis thereof.

3. A device in accordance with claim 2 wherein the hemispherical end of said valve body intersects a portion of the wall of said conduit at said aperture sufficiently to form a valve seat with said conduit wall and a liquid and bacterial seal around said aperture.

4. A device in accordance with claim 3 further comprising a cap over the open end of said housing and compression means thereunder retaining said valve body in a seated condition in said housing, and an orifice in said cap for receiving a catheter, said orifice being in the form of a curvilinear slot having a length less than a full circle and a width approximating the outer diameter of the catheter, whereby the catheter after being inserted therethrough and into said valve body may be utilized for rotating said valve body between the positions of alignment and non-alignment of said aperture and said port within the bounds of said orifice.

5. A device in accordance with claim 4 wherein said compression means includes bacterial seal means to prevent invasion of bacteria between said valve body and said housing.

6. A device in accordance with claim 1 wherein said biologically compatible material is carbon.

7. A device in accordance with claim 1 wherein said housing is made of a metal selected from the group consisting of titanium, stainless steel and a chromium-cobalt alloy and is coated with carbon, wherein said valve body comprises a graphite core and a coating of carbon on said core, and wherein said conduit is made of pyrolytic carbon.

8. A device in accordance with claim 1 further comprising a carbon flange around the perimeter of said housing, said flange having a plurality of holes therethrough, whereby body tissue will grow in and around said holes and will stabilize the position of the device when utilized in a living body.

9. A device in accordance with claim 1 wherein the inner portion of said housing is tapered toward the closed end and said valve body within said housing is formed at least on its outer surface complementary to the tapered inner portion of said housing in a close-fitting relation.

10. A device in accordance with claim 9 wherein said housing adjoins said conduit at the side of said housing near the closed end thereof, and wherein the tapered end of the valve body intersects a portion of the wall of said conduit at said aperture sufficiently to form a valve seat with said conduit wall and a liquid and bacterial seal around said aperture.

11. A device in accordance with claim 10 further comprising a cap over the open end of said housing and compression means thereunder retaining said valve body in a seated condition in said housing, an orifice in said cap, and a boss eccentrically located on the outer end of said valve body and projecting through the orifice of said cap for gripping to rotate said valve between the positions of alignment and non-alignment of said aperture and said port.

12. A device in accordance with claim 11 wherein said compression means includes bacterial seal means to prevent invasion of bacteria between said valve body and said housing.

* * * * *